(12) United States Patent
Harrison et al.

(10) Patent No.: US 9,551,668 B2
(45) Date of Patent: Jan. 24, 2017

(54) MICROPLASMA FOR DOWNHOLE COMPOSITIONAL ANALYSIS

(75) Inventors: Christopher Harrison, Auburndale, MA (US); Neil Bostrom, Salt Lake City, UT (US); Bradley Kaanta, Cambridge, MA (US)

(73) Assignee: SCHLUMBERGER TECHNOLOGY CORPORATION, Sugar Land, TX (US)

( * ) Notice: Subject to any disclaimer, the term of this patent is extended or adjusted under 35 U.S.C. 154(b) by 988 days.

(21) Appl. No.: 13/549,135

(22) Filed: Jul. 13, 2012

(65) Prior Publication Data
US 2013/0014943 A1 Jan. 17, 2013

Related U.S. Application Data

(60) Provisional application No. 61/508,159, filed on Jul. 15, 2011.

(51) Int. Cl.
| | |
|---|---|
| *E21B 49/10* | (2006.01) |
| *G01N 21/66* | (2006.01) |
| *G01N 1/10* | (2006.01) |
| *G01N 1/40* | (2006.01) |
| *G01N 33/28* | (2006.01) |

(Continued)

(52) U.S. Cl.
CPC .............. *G01N 21/66* (2013.01); *G01N 1/10* (2013.01); *G01N 1/4022* (2013.01); *G01N 33/2823* (2013.01); *E21B 2049/085* (2013.01); *G01N 21/68* (2013.01)

(58) Field of Classification Search
CPC ........ E21B 49/10; E21B 47/024; E21B 47/00; G01V 11/00
USPC .......... 73/152.24, 152.23, 152.02, 23.41, 73/152.07, 152.09, 152.11, 152.18, 73/152.01; 166/264, 66
See application file for complete search history.

(56) References Cited

U.S. PATENT DOCUMENTS

| | | | |
|---|---|---|---|
| 6,270,687 | B1 | 8/2001 | Ye et al. |
| 7,123,361 | B1 | 10/2006 | Doughty |

(Continued)

FOREIGN PATENT DOCUMENTS

| | | |
|---|---|---|
| GB | 2462906 A | 3/2010 |
| WO | 2009064557 A1 | 5/2009 |

OTHER PUBLICATIONS

Bass et al., "A capacitively coupled microplasma (CCµP) formed in a channel in a quartz wafer," J. Anal. At. Spectrom., 2001, vol. 16: pp. 919-921.

(Continued)

*Primary Examiner* — Lisa Caputo
*Assistant Examiner* — Nigel Plumb
(74) *Attorney, Agent, or Firm* — Jakub Michna

(57) ABSTRACT

An apparatus and method for elemental analysis of a formation fluid from a subsurface tool having a housing, a sampling probe for collecting a sample of the formation fluid external to the housing, and a microplasma device within the housing and in fluid communication with the sampling probe. The microplasma device includes an upstream gas system, a sampling valve in fluid communication with the sampling probe and the upstream gas system, an expansion chamber for volatizing the formation fluid sample obtained from the sampling valve, and a microplasma chamber in fluid communication with the expansion chamber for ionizing the volatilized fluid sample.

20 Claims, 4 Drawing Sheets

(51) Int. Cl.
*E21B 49/08* (2006.01)
*G01N 21/68* (2006.01)

(56) References Cited

U.S. PATENT DOCUMENTS

| | | | | |
|---|---|---|---|---|
| 7,384,453 | B2* | 6/2008 | Bostrom | G01N 30/32 |
| | | | | 73/23.42 |
| 7,460,225 | B2* | 12/2008 | Karanassios | G01N 21/67 |
| | | | | 356/246 |
| 7,733,490 | B2* | 6/2010 | Goodwin | E21B 49/10 |
| | | | | 166/250.01 |
| 2004/0178917 | A1 | 9/2004 | Duan | |
| 2007/0068242 | A1 | 3/2007 | DiFoggio | |
| 2009/0151426 | A1* | 6/2009 | Shah | E21B 47/10 |
| | | | | 73/23.35 |

OTHER PUBLICATIONS

Eijkel et al., "A dc Microplasma on a Chip Employed as an Optical Emission Detector for Gas Chromatography," Anal. Chem., Jun. 2000, vol. 72(11): pp. 2547-2552.

Iza et al., "Low-Power Microwave Plasma Source Based on a Microstrip Split-Ring Resonator," IEEE Transactions on Plasma Science, Aug. 2003, vol. 31(4): pp. 782-787.

Karanassios, "Microplasmas for chemical analysis: analytical tools or research toys?" Spectrochimica Acta Part B, 2004, vol. 59: pp. 909-928.

Yoshiki et al., "Capacitively Coupled Microplasma Source on a Chip at ATmospheric Pressure," Jpn. J. Appl. Phys. Part 2, Apr. 2001, vol. 40(4A): pp. L360-L362.

\* cited by examiner

MICROPLASMA FOR DOWNHOLE COMPOSITIONAL ANALYSIS

CROSS-REFERENCE TO RELATED APPLICATION

This application claims benefit of U.S. Provisional Patent Application Ser. No. 61/508,159 filed Jul. 15, 2011, which is incorporated herein by reference in its entirety.

BACKGROUND

Hydrocarbon producing fields typically include a subterranean fluid that is comprised of a mixture of oil, gas and water, wherein the phase relationship between these components are controlled by the pressure, temperature and composition of the fluid. It is desirable to analyze and evaluate these fluids to determine fluid characteristics of commercial interest to the petroleum industry, such as the type and quality of the components within the reservoir. One way to accomplish this is by retrieving a sample of the subterranean formation fluid to the surface and analyzing the fluid to determine its composition.

SUMMARY

This summary is provided to introduce a selection of concepts that are further described below in the detailed description. This summary is not intended to identify key or essential features of the claimed subject matter, nor is it intended to be used as an aid in limiting the scope of the claimed subject matter.

In one aspect, embodiments disclosed herein relate to an apparatus for elemental analysis of a formation fluid from a subsurface tool. The tool includes a housing, a sampling probe for collecting a sample of the formation fluid external to the housing, a microplasma device within the housing and in fluid communication with the sampling probe. The microplasma device includes an upstream gas system having a gas flow element for controlling a carrier gas flow throughout the microplasma device, a sampling valve in fluid communication with the sampling probe and the upstream gas system. The microplasma device also includes an expansion chamber for volatizing the formation fluid sample obtained from the sampling valve and a microplasma chamber in fluid communication with the expansion chamber for ionizing the volatilized fluid sample.

In another aspect, embodiments disclosed herein relate to a downhole tool for estimating composition of a fluid downhole. The downhole tool includes a probe configured to extract fluid from a formation, a microplasma device configured to generate microplasma from the fluid, at least one sensor in communication with the microplasma generated downhole by the microplasma device, and a spectrometer including a processor configured to analyze output from the at least one sensor to estimate the composition of the fluid downhole.

In another aspect, embodiments disclosed herein relate to a method for estimating composition of a fluid downhole. The method includes collecting a fluid sample from a formation by a downhole tool, volatilizing the fluid sample downhole, inducing microplasma in the volatilized fluid sample downhole, collecting emission from the plasma by a sensor, and analyzing signals from the sensor using a processor to estimate the composition of the fluid downhole.

Other aspects and advantages of the invention will be apparent from the following description and the appended claims.

DETAILED DESCRIPTION

Figure 1:
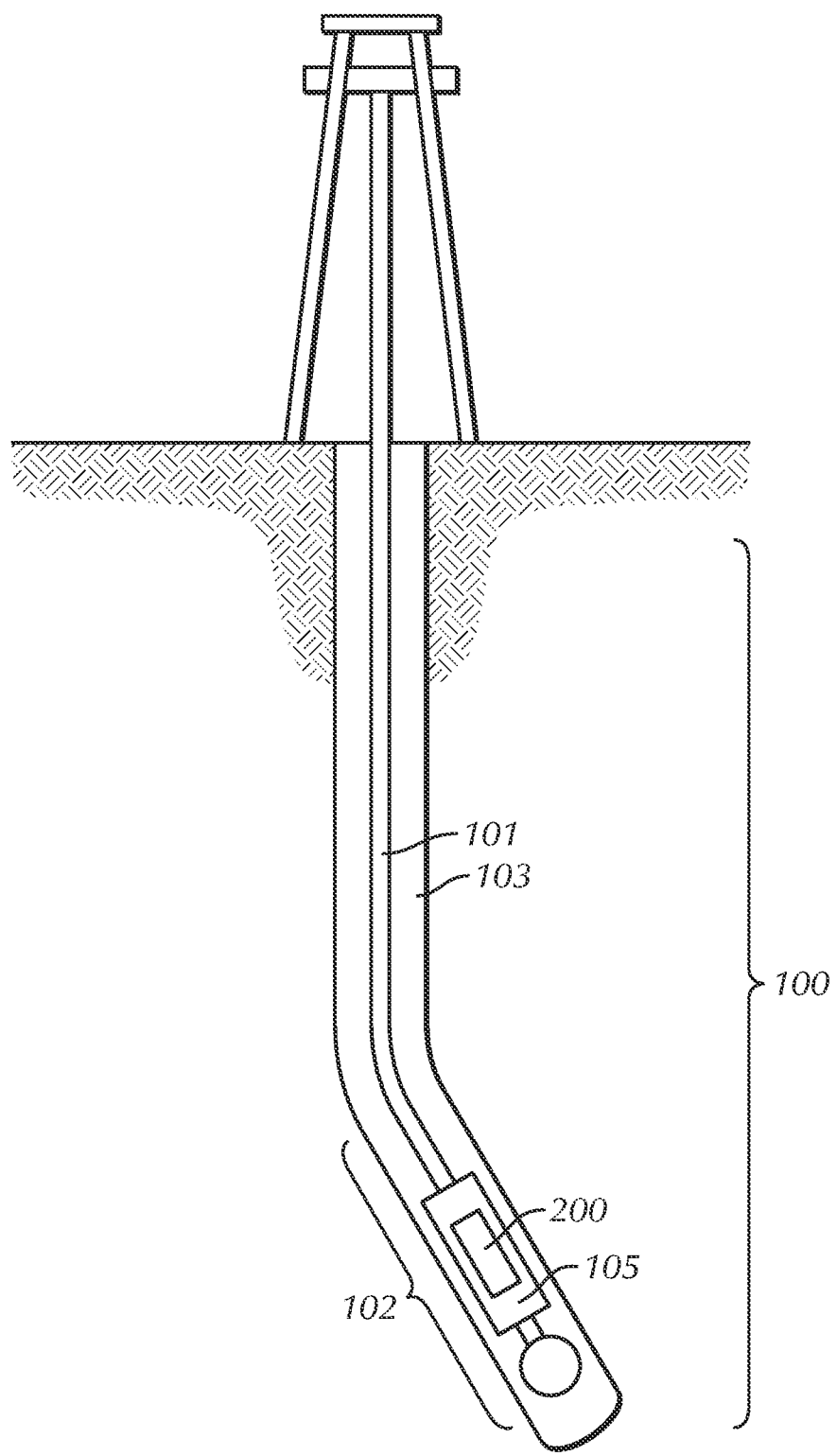
FIG. 1 is a schematic illustration of a drilling system in accordance with embodiments disclosed herein.

In the various embodiments, numerous specific details are set forth in order to provide a more thorough understanding of the present disclosure. However, it will be apparent to one of ordinary skill in the art that the details of the present disclosure may be practiced without these specific details. In general, the present disclosure relates to an apparatus and method of performing compositional and elemental analysis downhole using a microplasma device.

The example methods and apparatus described herein may be used to analyze fluids from a subsurface formation or a wellbore using a microplasma device. In particular, the example methods and apparatus described herein to analyze downhole fluids involve obtaining a fluid sample, volatilizing a portion or all of the fluid sample to a gaseous phase (e.g., by decreasing the density or pressure of the fluid sample), ionizing the sample by passing the volatilized sample through a microplasma chamber, and analyzing the resulting ionized sample by a spectroscopic method downhole. In the illustrated examples described herein, fluid samples may be ionized by moving the samples through a microplasma chamber and exposing the samples to an ionizing environment in the microplasma chamber. The analyses described herein may be performed substantially downhole or partially downhole and partially uphole (i.e., at ground level).

The example methods and apparatus described herein may be used to analyze a fluid sample from a formation fluid by ionizing a fluid sample by using a microplasma device. Plasmas often use high voltages for ignition. High voltages may be hard to control, especially if the voltage is being provided to an oilfield tool where the voltage may be unstable and potentially dangerous.

As understood to those of ordinary skill in the art, "plasma" refers to a state of matter similar to a gas in which a certain portion of the particles are ionized. In accordance with the present disclosure, ionization may occur when a fluid sample enters the microplasma chamber, i.e., the atoms and molecules of the volatilized fluid sample are bombarded with electrons due to the arrangement of the microplasma chamber. Based on this ionization, an analysis of the fluid sample may be performed. For example, the bombardment of the atoms in the fluid sample may cause the atoms to emit photons having respective wavelengths as the atoms return to their lower energy levels (i.e., their energy levels prior to the excitement). The wavelengths of the photons may be measured using a spectrometer to determine the presence of particular atoms corresponding to those wavelengths. Spectroscopic methods may then be used to accurately identify atoms, molecules, substances or fluid components such as, but is not limited to mercury, nickel, vanadium, sulfur, radon, polonium, barium, strontium, nitrogen, calcium, oxygen, helium, methane, ethane, propane, etc. in fluid samples and the concentrations of those atoms, molecules, substances, or fluid components and/or atomic concentrations. The intensity of the emitted wavelengths or the size-to-mass ratio (in the case of mass spectrometry) may be measured to determine the concentrations of those atoms. In addition to determining atomic concentration(s), detecting the presence of a particular atom in a fluid sample may be indicative of the presence of a particular molecule. For example, detecting the presence and concentration of sulfur (S) atoms can be indicative of the presence and concentration of hydrogen sulfide ($H_2S$) in a fluid sample as well as other thiols (mercaptans, hydrosulfides, thiolates, mercaptides) that are sufficiently volatile to vaporize into the gaseous portion of the depressurized sample.

As illustrated in FIG. 1, a drilling system (100) includes a bottom hole assembly (102) connected at the bottom end of a drill string (101) suspended within a wellbore (103). One or more other downhole tools may be located along the drill string (101) or along a wireline in the wellbore when the drill string (101) and bottom hole assembly (102) are removed from the well. Further, in accordance with one or more embodiments, a microplasma device (200) may be contained within a downhole tool (105) which may be located along the drill string (101), on a wireline (not shown) or within a downhole tool (not shown). The microplasma device (200) may be electrically connected to a component of a motor (not shown) or a battery (not shown) to receive energy therefrom. It should be understood that no limitation is intended by the arrangement of the drilling system, including the presence of absence of one or more components. As mentioned above, it is also envisioned that the drill string (101) may also be replaced by structures such as a wireline or any other apparatuses to convey the microplasma device (200) into the wellbore, where the microplasma device (200) is electrically connected to one or more tools located on the wireline.

Figure 2:
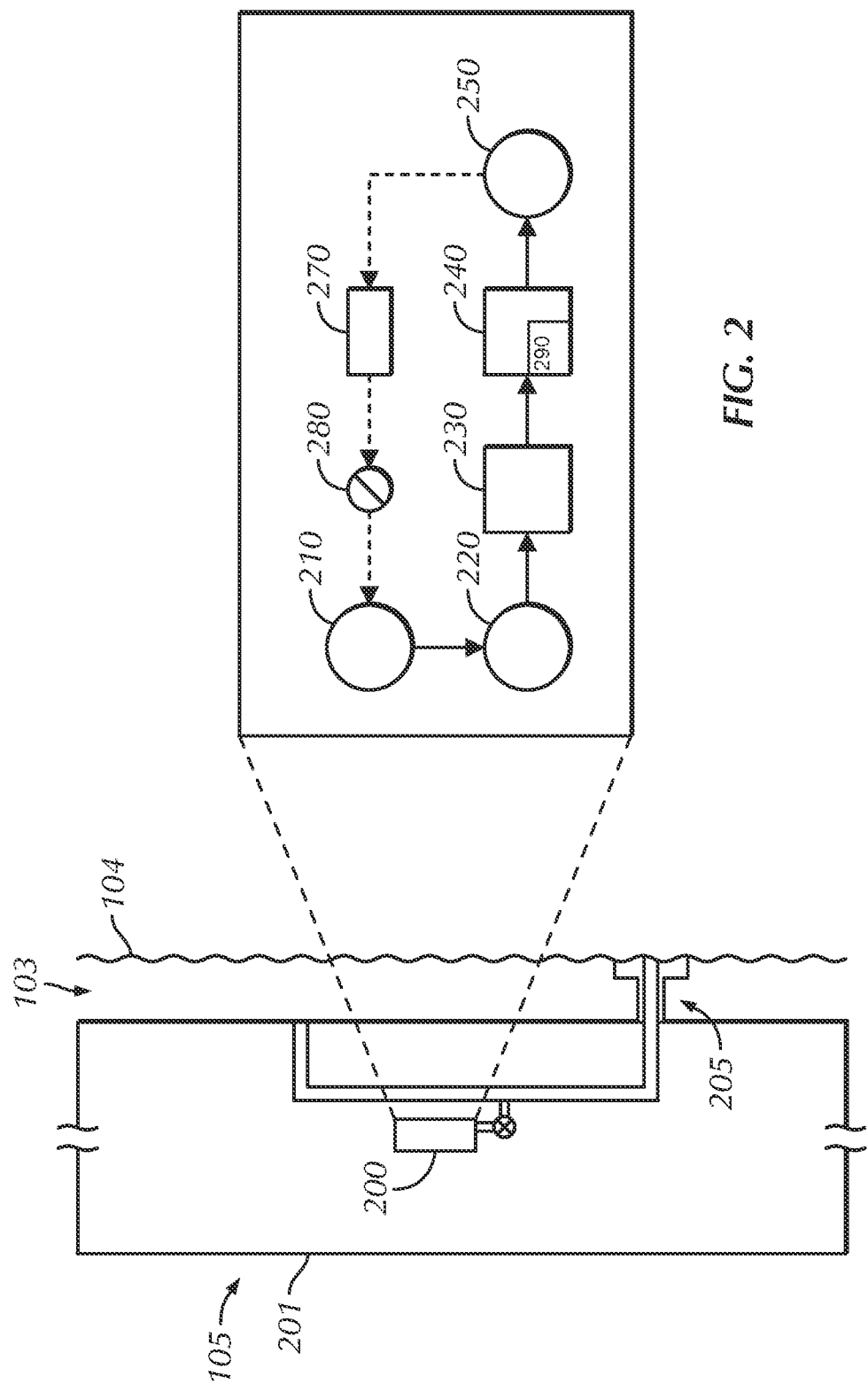
FIG. 2 is a schematic illustration of a downhole compositional system used in accordance with embodiments disclosed herein.

FIG. 2 illustrates a microplasma device (200) within the downhole tool (105) in a downhole environment. The downhole tool (105) includes a housing (201) that houses the microplasma device (200). The microplasma device (200) may be fluidly coupled to a sampling probe (205) to extend the sampling probe (205) into engagement with the subterranean formation (104) to enable drawing formation fluid samples via the sampling probe (205). It should be understood that the fluid sample to be drawn into for analysis by the microplasma device (200) may also be taken from the wellbore (103) or from a production flowline (not shown). One example of a sampling probe includes that described in U.S. Pat. No. 7,733,490; however, no limitation exists on the type of sampling probe (205) to be used in conjunction with the microplasma device (200) of the present disclosure. Upon collection of a formation fluid sample, the sample may be fed into the microplasma device (200) via sampling valve (220).

The sampling valve (220) conveys fluids from the wellbore to the expansion chamber (230) at a rate determined by the upstream gas system (210) (described in greater detail below). Thus, the sampling valve (220) may be in fluid communication with the sampling probe (205), the upstream gas system (210) and the expansion chamber (230). Examples of sampling valve (220) may include a rotary valve manufactured by VALCO® or RHEODYNE®. The sampling valve (220) may be any device which will rapidly transfer the formation fluid sample into the expansion chamber (230). The sampling valve may be, but is not limited to, a series of needle valves, a metering valve, an injection valve or any such device known to one skilled in the art. In some embodiments, either upstream or downstream of the sampling valve (220), but prior to the sample being fed to the microplasma device (200), the sample may be sent through a filtering device to remove any particulates or water that may be in the sample. The filtering device may be any one of membranes, sorbents, zeolites, wire screens, wire mesh or combinations thereof.

In the expansion chamber (230), fluid samples may be heated to moderate temperatures (<200° C.) to volatilize low boiling components or heated to high temperatures (about 300° C. and greater) to volatilize the entire sample. The expansion chamber (230) may optionally be filled with glass wool to aid in vaporization or to reduce the migration of liquid and/or non-volatile components into the downstream microplasma chamber (240). Upon volatilization of the fluid sample, an aliquot of vapor may be carried into the microplasma chamber (240) for ionization. Thus, the expansion chamber (230) may be in fluid communication with the microplasma chamber (240) via tubing, which may feed the sample to the microplasma chamber (240) where the volatilized sample may be ionized.

Figure 3:
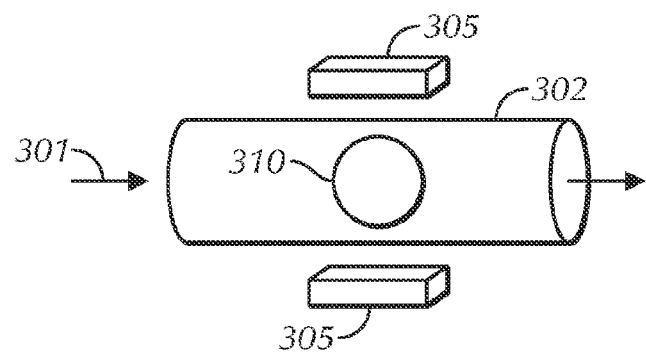
FIG. 3 is a schematic illustration of a microplasma chamber in accordance with embodiments disclosed herein.

Referring now to FIG. 3, a schematic of the interior of a microplasma chamber is shown. As shown in FIG. 3, a volatilized fluid sample (301) traverses through the microplasma chamber (not shown) in a tube (302). In some embodiments, the internal volume of the microplasma chamber (not shown) may be about 1 microliter or less. In some embodiments, the microplasma chamber (not shown) may have an internal dimension, such as the widest part of the microplasma chamber, of about one millimeter or less. As the volatilized fluid sample (301) passes between electrodes (305) (specifically, an anode and a cathode), an applied electrical potential difference between the electrodes (305) may cause ionization of the volatilized fluid sample (301) in the section of the tubing (302) between the electrodes (305). In one or more embodiments, the electrodes (305) may be spaced apart by a distance up to 1 mm, but may be less than 500 microns or less than 300 microns in other embodiments. In other embodiments, the electrodes (305) may be spaced apart by a distance ranging from about 50 to about 500 microns. Further, while the electrodes (305) are illustrated as being external to the tubing (302), it is also within the scope of the present disclosure that the electrodes (305) may be placed inside or on the external surface of the tubing (302). It is also within the scope of the present disclosure that a split ring resonator may be incorporated therein to reduce the amount of power necessary to ionize the gaseous sample and generate the plasma. Further, in one or more embodiments, the microplasma chamber may be fabricated to be part of a monolithic device.

The microplasma chambers of the present disclosure may use electrodes possessing high electrical conductivity and ductility such as, but not limited to, copper, gold, platinum, nickel, molybdenum, tungsten, doped semiconductors or mixtures thereof. Generally, materials with "high electrical conductivity" are materials wherein the Fermi level lies in the conduction band giving rise to free conduction electrons.

In some uses, platinum and nickel may offer good corrosion resistance as they do not sputter easily due to the energetic ion bombardment of plasma generation and can be used for direct current sources. Refractory metals such as molybdenum and tungsten may also be used due to their high melting points.

In order to generate microplasmas, dielectric materials may be present in the microplasma chamber, through which an electric current is applied. In one or more embodiments, the dielectric material may be present in the form of the tubing, i.e., through the use of a dielectric tubing. Commonly used dielectric materials may include, but are not limited to, glass, mica, sapphire, and various ceramic oxides (such as silica, alumina). In one or more embodiments, when the dielectric material is integrated with the tubing, the selection of the tubing material may be based on one or more factors including optical transparence, corrosion resistance, thickness (based in part on the operating pressure within the tool and ability to reduce the wall thickness to allow for low power requirements to generate the plasma).

Further, it is also intended that any known configurations of components (electrodes, dielectric materials, etc.) may be used to generate microplasma in the microplasma chamber (240). The term "microplasma" refers to discharges with dimensions that range from one micrometer up to 5 millimeters. Microplasmas or cold plasmas may be ignited and operated with power sources consuming no more than a 10 watts of power in a gap between electrodes separated by less than 1000 microns. In some embodiments, the microplasma may be termed a low power plasma which allows for operation at low voltages ranging, for example, from about 0.1 to about 10 volts. In some embodiments, the low voltages may be less that 10 volts, less than 5 volts, about 1 volt, or less than 1 volt. These plasmas can be ignited at pressures up to and above atmospheric pressure in capillaries or microchannels. Discharges of microplasma may create a highly reactive environment that contains charged particles, excited species, radicals and photons.

Further, different types of microplasmas may be classified into three modes: concentrated energy mode, space-limited mode, and mass limited mode. In concentrated energy mode, a microplasma is generated at electrode tips with concentrated high electric field strengths and thus, high electrical energy. In space limited mode, the microplasma volume is limited by solid boundaries such as microcells or capillaries. Finally, in mass limited mode, a microdischarge develops between electrodes using an initial material such as a powder or droplet with no surrounding walls. As such, one skilled in the art can appreciate the different configurations that are available and may employ different strategies to determine which configuration may be used to generate microplasmas in accordance with the embodiments disclosed herein depending on the particular application.

Microplasma sources may also be classified by the frequency of excitation and the electrode configuration, following a typical classification for plasmas. Examples of microplasma classifications include, but are not limited to, a cathode boundary layer (CBL) microplasma, a dielectric barrier discharge (DBD) microplasma, a capillary plasma electrode discharge (CPED) microplasma, a micro-hollow cathode discharge (MHCD) microplasma, a radio frequency inductively coupled (RFIC) microplasma, a radio frequency capacitively coupled (RFCC) microplasma, and a microstrip (MS) microplasma. It is within the scope of the present disclosure that any of such electrode/dielectric arrangements may be used to generate the microplasma in accordance with the present disclosure. A CBL is a direct current (DC) glow discharge and consists of a cathode in a planar shape and a ring-shaped anode. In this configuration, a discharge is restricted to the cathode. A DBD microplasma is a discharge which uses dielectric boundaries to prevent the discharge to transit into an arc by preventing charges to be absorbed at the electrodes. A DBD configuration consists of a dielectric material around two electrodes coated with an insulating layer. The two electrodes have an air gap between them and a plasma may be generated at frequencies that as low as several kilohertz to greater than 20 megahertz. CPED use dielectric capillaries to cover one or both electrodes allowing the dielectric material to suppress the glow-to-arc transition by stabilizing the cathode region of the plasma. A MHCD has two closely spaced hollow electrodes separated by a dielectric layer with a voltage applied between them. The MHCD may be operated at a positive current-voltage, which may be used in parallel operation with other devices without the use of ballast resistors. MHCD plasmas are stable at atmospheric pressures. RFIC microplasmas are electrode-less discharges which utilize induction through a coil wrapped around a dielectric wall to generate microplasmas parallel to the dielectric material, thus minimizing sputtering which generally prohibits prolonged usage of microplasmas. RFCC microplasmas use the same configuration as an RFIC microplasma, however, the electric field is perpendicular to the dielectric. MS microplasmas transfer electromagnetic fields into a small air gap in order to generate a microplasma. One embodiment of an MS microplasma may be a split-ring resonator be used to ignite and sustain a wide discharge microplasma. In one or more embodiments, low frequency operations, such as direct current (DC) or alternating current (AC) may be used to provide for using low-cost electronics. Alternatively, high frequencies such as radio and microwaves, may result in more efficient plasma generation. In some embodiments, the excitation frequency of the microplasma may be about 1 gigahertz. Microplasmas having excitation frequencies of about 1 gigahertz may dissipate about 1 watt of power. In some embodiments, operating the microplasma at high frequencies may minimize erosion in plasmas created with a constant or DC voltage.

After a volatilized fluid sample (301) has been ionized in the microplasma chamber (240), the sample may be analyzed by a detection/spectroscopic system (290) in the microplasma chamber (240). For example, the microplasma chamber (240) may include a detection system (290) such as, but not limited to, an atomic absorption spectrometer, an atomic emission spectrometer or a mass spectrometer, a Visible-Ultra Violet (UV-vis) spectrometer, a Fourier transform infrared (FTIR) spectrometer, a Raman spectrometer, or a fluorescence spectrometer. The detection system (290) may be a single or a multi-channel detector assembly, and may include any arrangement known in the art. In one or more particular embodiments, the microplasma generated in the microplasma chamber (240) may be analyzed by emission spectroscopy as it requires only the measurement of the emission intensity at one or several wavelengths. Further, while not shown, in one or more embodiments, the detection system (290) may be set substantially orthogonal to the flow path through the microplasma chamber (240). That is, in relation to the arrangement illustrated in FIG. 3, the detector (290) may be aligned on a plane substantially perpendicular to that shown in FIG. 3. Thus, as the plasma is generated, detection and analysis of the plasma may occur while the plasma is still within the microplasma chamber (240). However, the present disclosure is not so limited, and the detection system may be located in any location within the system. For example, in one or more embodiments, the detection system may be aligned in series with and downstream with respect to electrodes (305).

In one or more embodiments, the detection system (290) may measure other characteristics of the ionized sample. The resistivity of the ionized sample may be measured between the electrodes of the microplasma chamber (not shown). For example, the resistivity of the ionized sample may be observed for a selected frequency or a range of selected frequencies. The detection of such resistivity changes may indicate the presence of different species in the formation fluid, and may be used along with a calibration table to determine a concentration of a given element or elements present in the fluid sample. Specifically, as the atom or molecules in a formation fluid are ionized within the microplasma chamber, the electrons of the atom or molecule may be excited to a higher energy level, thereby causing an electronic transition. The resulting electronic transition ionizes the atom or molecule in the formation fluid causes the resistivity to decrease and can thereby be correlated to a given concentration of a particular atom or molecule.

The detection system may include one or more sensors to measure the fluid samples after being ionized, i.e., to measure the plasma sample. For example, if the sensor is to measure resistivity characteristic changes in plasma samples before and/or after ionization, the sensor can be provided with resistivity measurement units (e.g., ohmmeters). Alternatively, if the sensor is to measure spectroscopic characteristics of plasma samples, the sensor can be implemented using one or more spectrometers configured to measure a single wavelength (e.g., a wavelength parameter) or a plurality of wavelengths (e.g., a plurality of wavelength parameters). That is, if a plasma is analyzed to identify the presence and concentration of only a single type of molecule (e.g., a hydrogen sulfide ($H_2S$) molecule) in fluid samples, the spectrometer(s) of the detection system may be configured to measure a wavelength corresponding to an atom (e.g., a sulfur (S) atom) present in the molecule of interest. In one or more embodiments, if a plasma sample is analyzed to identify the presence and concentration of a plurality of molecules in a sample, the spectrometer(s) of the sensor may be configured to measure a plurality of wavelengths corresponding to atoms (e.g., sulfur (S) atoms, mercury atoms, nickel atoms, etc.) present in those molecules of interest. In any case, the parameter measurement values obtained using the sensor may be used to identify particular atoms or molecules present in samples based on models for those atoms or molecules produced microplasma chamber.

In one or more embodiments, the sensor may be implemented in connection with an optical spectrometer or a resistivity measurement unit. However, in other example implementations, the sensor may be implemented by any suitable plasma measurement unit. Further, although the downhole tool is provided with one sensor, in other example implementations, any number of plasma sensors (e.g., 2, 3, etc.) may be used that may measure one or more parameters of the plasma sample after ionizing the volatilized fluid sample.

Also included in the microplasma device (200) is an upstream gas system (210) and a downstream gas system (250), which together may allow for the microplasma device of the present disclosure to be self-contained. Upstream gas system (210) and downstream gas system (250) operate to supply a stream of carrier gas through the microplasma chamber (240), i.e., to carry the fluid sample into the expansion chamber (230) and the volatilized fluid sample into the microplasma chamber (240) and also assist in purging microplasma chamber (240) of any gas or plasma therein. As shown in FIG. 2, the upstream gas system (210) and downstream gas system (250) may optionally be in fluid connection with a recirculation line extending therebetween. In the event of recirculation, a pump (270) and filter (280) may optionally be included between the upstream gas system (210) and the downstream gas system (250) for recirculation and filtration. Thus, microplasma device (200) may be configured to be self-contained such that the outlet (not shown) of the upstream gas system (210) is in flow communication with the inlet (not shown) of the downstream gas system (250) via expansion chamber (230) and the microplasma chamber (240) and such that the outlet (not shown) of the downstream gas system (250) is in flow communication with the inlet (not shown) of the upstream gas system (210) via the pump (270) and the filter (280).

The upstream gas system (210) is generally directed at controlling the rate of a gas flow through the microplasma device (200). The rate of gas flow may be controlled through a variety of methods or devices, such as pressure regulators, flow pumps, and/or a "pressure reservoirs." In some embodiments, the handling of the gas after traversing the plasma chamber (240) may also include a variety of methods and/or devices, such as a filter, a waste vessel, a flow line for expelling used gases, and/or a gas purification device, such as an oxidation or electrolysis device.

One approach that may be used to maintain a desired rate of gas flow through the microplasma device (200) may involve using a "pressure reservoir" or isobaric (constant pressure) reservoir that is at least partially comprised of a class of materials that controllably adsorbs/desorbs a carrier gas, such as hydrogen. This class of materials may include any material and/or combination of materials suitable to the desired end purpose, such as a powdered and/or sintered metal hydride material. Another approach that may be used to maintain a desired rate of carrier gas flow through a microplasma device (200) may involve using an oxidation cell to maintain a low pressure at the downstream end of the microplasma chamber (240) by burning the effluent (the analyte and a carrier gas, such as hydrogen) from the microplasma chamber. However, other means of controlling the pressure and flow through the microplasma chamber (240) known in the art may be used, similar to those described in U.S. Pat. No. 7,384,453, which is assigned to the present assignee and herein incorporated by reference in its entirety.

Further, as indicated above, and as illustrated in FIG. 2, the microplasma device (200) may be contained within a housing (201) as part of the downhole tool (105). The housing (201) may be of any shape, including cylindrical and may contain the above-mentioned upstream gas system (210), high pressure sampling valve (220), expansion chamber (230), microplasma chamber (240), and downstream gas system (250). In various embodiments, the housing protects (e.g., seals) the microplasma device (200) from an exterior environment (e.g., the borehole environment). The particular material used to form the housing is of no limitation on the scope of the present disclosure. The housing may be selected to be sufficiently capable of withstanding the high G-forces, temperatures (e.g., at least 150° C.), pressures (e.g., at least 15,000 psi), and corrosive environments experienced downhole within the wellbore. Alternative housing compositions may employ titanium, carbon reinforced alloys, and any other alloys, solid solutions or intermetallics that can retain structural integrity within the downhole environment.

In one or more embodiments, the upstream gas system (210) may contain a carrier gas, which may also serve as a purge gas to remove the volatized sample from the microplasma chamber or may be used to create or maintain the plasma. The selection of the gas may be based, in part, on expected downhole temperatures. For example, at moderate temperatures "zero air" pure helium or helium with a small amount of oxygen may be used as a purge gas, while at higher temperatures other inert gases such as Ne, Ar, Xe, etc., may be used alone or in combination with He. In some embodiments, the selection of the gas to create a plasma should minimize the amount of energy necessary to generate the plasma. The gas may become part of the plasma. In some embodiments, the gas may help ionize atoms, thereby permitting the atoms to provide an optical emission for detection.

To control or collect data from the detection system, the downhole tool may be provided with a downhole control and data acquisition system (not shown). Although not shown, the downhole control and data acquisition system may include a processor, one or more memories and a communication interface (e.g., a modem). The communication interface of the downhole control and data acquisition system may be communicatively coupled to a surface system to communicate analysis data and/or receive control data. The wires or lines may include a databus (e.g., carrying digital information and/or analog information), electrical power lines, etc. and may be implemented using a single conductor or multiple conductors.

To store reference measurement values of reference formation fluids known to have particular fluid compositions, the downhole control and data acquisition system may store or be communicatively coupled to a reference database. The reference measurement values may be used to identify fluid compositions of subsequently measured formation fluid samples. In some example implementations, the reference database may be additionally or alternatively stored in a surface data acquisition system.

Figure 4:
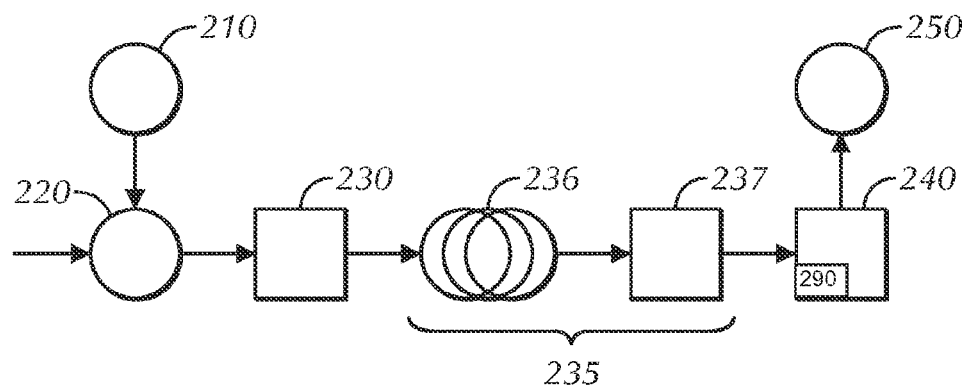
FIG. 4 is a schematic illustration of a downhole compositional system in accordance with embodiments disclosed herein.
Figure 5:
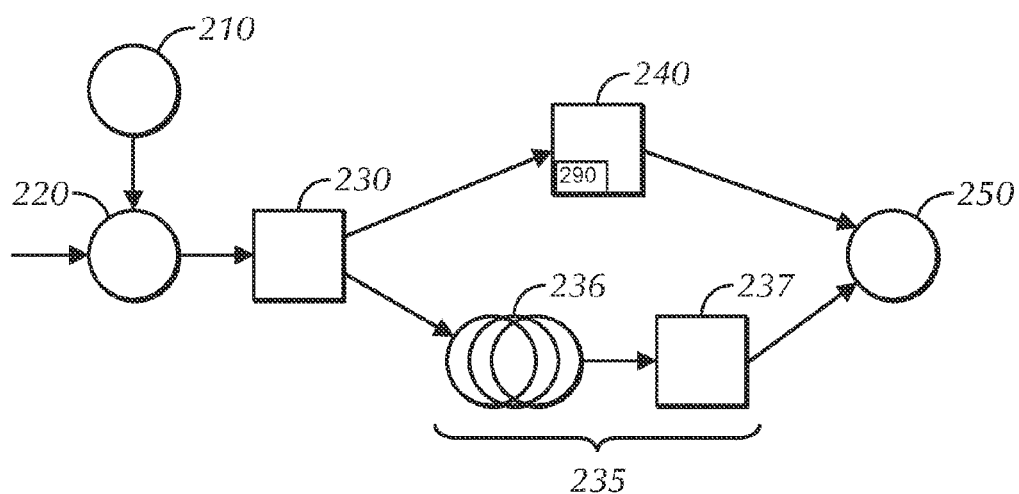
FIG. 5 is a schematic illustration of a downhole compositional system in accordance with embodiments disclosed herein.

Referring now to FIGS. 4-5, additional configurations of a microplasma device used in one or more embodiments is shown. Specifically, as shown in FIGS. 4-5, a gas chromatography system (235) may also be incorporated into the microplasma device (200). FIG. 4 shows a schematic wherein the gas chromatography system (235) is used in series with the microplasma chamber (240). In various embodiments, the microplasma chamber (240) also includes a detection system (290). Specifically, after a fluid sample is volatilized in the expansion chamber (230), it may be passed through a gas chromatography system (235) including a gas chromatography column (236) and a detector (237), prior to reaching the microplasma chamber (240). Similar to FIG. 2, a fluid sample is fed to expansion chamber (230) via sampling valve (220), which is in fluid communication with a sampling probe (not shown) and a upstream gas system (210). Further, also similar to FIG. 2, a downstream gas system (250) is downstream from the microplasma chamber (240) and may assist in purging a sample from the microplasma chamber (240).

In contrast, FIG. 5 shows a schematic wherein the gas chromatography system (235) is in parallel with the microplasma source (240), thus being in fluid contact with the expansion chamber (230) and the downstream gas system (250). Specifically, after a fluid sample is volatilized in the expansion chamber (230), a portion may be passed through a gas chromatography system (235) including a gas chromatography column (236) and a detector (237), and a second portion may be passed through the microplasma chamber (240). It is also within the scope of the present disclosure that an entire sample may be passed to one or the other of the gas chromatography system (235) and the microplasma chamber (240), or that the volatilized fluid sample may be pulsed between the two. Similar to FIG. 2, a fluid sample is fed to expansion chamber (230) via sampling valve (220), which is in fluid communication with a sampling probe (not shown) and a upstream gas system (210). Further, also similar to FIG. 2, a downstream gas system (250) is downstream from the microplasma chamber (240), as well as the gas chromatography system (235) and may assist in purging a sample from either or both of the microplasma chamber (240) and gas chromatography system (235).

Various gas chromatography systems, as known in the art, may be used in conjunction with the microplasma device of the present disclosure. However, in one or more embodiments the gas chromatography system may include a self-contained system similar to that described in U.S. Pat. No. 7,384,453, which is assigned to the present assignee and herein incorporated by reference in its entirety.

In one or more embodiments, the combination of the microplasma chamber and the gas chromatography system may allow for broader evaluation of a fluid sample. For example, advantageously, the use of gas chromatography may allow for the separation of hydrocarbon components dependent on boiling point while the plasma generation may allow for identification of heteroatoms or non-hydrocarbon molecules.

Figure 6:
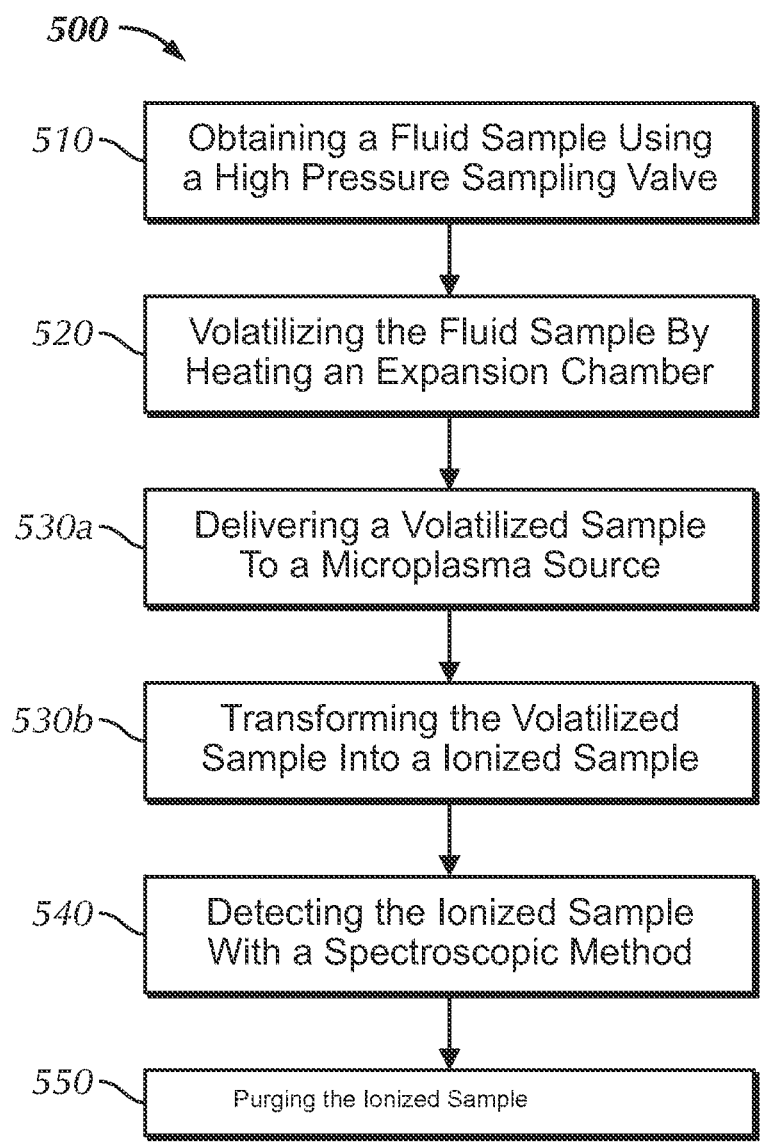
FIG. 6 is a schematic block illustration of a method for implementing a downhole compositional system in accordance with embodiments disclosed herein.

Referring to FIG. 6, a block diagram illustrating a method (500) for implementing the microplasma device (200) is shown. The method (500) includes obtaining a fluid sample (510), volatilizing the fluid sample by heating an expansion chamber (520), delivering a volatilized sample with a carrier gas to a microplasma device (530a), applying a voltage to the microplasma device thereby ionizing the volatilized sample into an ionized sample (530b), detecting the ionized sample with a spectroscopic method in a downstream gas system (540); and purging the ionized sample from the device using a purge gas (550). Optionally, it is also intended that the volatilized fluid sample may be subjected to gas chromatograph prior to or simultaneous with the ionization of the volatilized sample. Further, upon purging the ionized sample, the carrier gas may be recycled through the system (upon filtration and removal of contaminants and the like) to carry further fluid samples through the system.

Although only a few example embodiments have been described in detail above, those skilled in the art will readily appreciate that many modifications are possible in the example embodiments without materially departing from Microplasma for Downhole Compositional Analysis. Accordingly, all such modifications are intended to be included within the scope of this disclosure as defined in the following claims. In the claims, means-plus-function clauses are intended to cover the structures described herein as performing the recited function and not only structural equivalents, but also equivalent structures. Thus, although a nail and a screw may not be structural equivalents in that a nail employs a cylindrical surface to secure wooden parts together, whereas a screw employs a helical surface, in the environment of fastening wooden parts, a nail and a screw may be equivalent structures. It is the express intention of the applicant not to invoke 35 U.S.C. §112, paragraph 6 for any limitations of any of the claims herein, except for those in which the claim expressly uses the words 'means for' together with an associated function.

The invention claimed is:

1. An apparatus for elemental analysis of a formation fluid from a subsurface tool comprising:
   a housing;
   a sampling probe for collecting a sample of the formation fluid external to the housing;
   a microplasma device within the housing and in fluid communication with the sampling probe, comprising:
      an upstream gas system comprising:
         a gas flow element for controlling a carrier gas flow throughout the microplasma device;
         a sampling valve in fluid communication with the sampling probe and the upstream gas system;
         an expansion chamber for volatizing the formation fluid sample obtained from the sampling valve; and
         a microplasma chamber in fluid communication with the expansion chamber for ionizing the volatilized fluid sample,
      wherein the microplasma device is configured to ionize the volatilized fluid sample by applying a voltage of 10V or less; and
   a filter configured to remove particulates from the fluid sample prior to the fluid sample entering the microplasma chamber.

2. The apparatus of claim 1, wherein the microplasma chamber further comprises: a detection system.

3. The apparatus of claim 2, wherein the detection system comprises a spectrometer selected from the group consisting of: an atomic absorption spectrometer, an atomic emission spectrometer, a fluorescence spectrometer, a Visible-Ultra Violet (UV-vis) spectrometer, a Fourier transform infrared (FTIR) spectrometer, a Raman spectrometer, and a mass spectrometer.

4. The apparatus of claim 1, wherein the microplasma chamber comprises an anode and a cathode.

5. The apparatus of claim 4, wherein the microplasma chamber further comprises a dielectric material disposed between the anode and cathode.

6. The apparatus of claim 1, wherein the microplasma chamber comprises a split ring resonator.

7. The apparatus of claim 1, further comprising: a gas chromatography system in fluid communication with the microplasma chamber.

8. The apparatus of claim 5, wherein the gas chromatography system is in parallel fluid communication with the microplasma chamber.

9. The apparatus of claim 5, wherein the gas chromatography system in series fluid communication with the microplasma chamber.

10. The apparatus of claim 1, further comprising a downstream gas system for purging the ionized sample from the microplasma chamber.

11. The apparatus of claim 1, wherein the microplasma chamber operates at a voltages ranging from about 0.1 to about 10 volts.

12. The apparatus of claim 10, further comprising: a recirculation line between the upstream gas system and the downstream gas system.

13. A downhole tool for estimating composition of a fluid downhole comprising:
    a probe configured to extract fluid from a formation;
    a microplasma device configured to generate microplasma from the fluid, wherein the microplasma device is configured to ionize the volatilized fluid sample by applying a voltage of 10V or less;
    a filter configured to remove particulates from the fluid sample prior to the fluid sample entering the microplasma chamber;
    at least one sensor in communication with the microplasma generated downhole by the microplasma device; and
    a spectrometer including a processor configured to analyze output from the at least one sensor to estimate the composition of the fluid downhole.

14. A method for estimating composition of a fluid downhole, comprising:
    collecting a fluid sample from a formation by a downhole tool;
    volatilizing the fluid sample downhole;
    inducing microplasma in the volatilized fluid sample downhole by applying a voltage of 10V or less to the fluid sample;
    filtering the fluid sample to remove particulates prior to applying the voltage to the fluid sample;
    collecting emission from the microplasma by a sensor; and
    analyzing signals from the sensor using a processor to estimate the composition of the fluid downhole.

15. The method of claim 14, further comprising: purging the induced microplasma using a purge gas.

16. The method of claim 14, further comprising subjecting the volatilized fluid sample to gas chromatography prior to inducing microplasma.

17. The method of claim 14, further comprising subjecting the volatilized fluid sample to gas chromatography simultaneous with inducing microplasma.

18. The apparatus of claim 1, wherein the microplasma has an internal volume of 1 microliter or less.

19. The apparatus of claim 4, wherein the anode is spaced apart from cathode by a distance of 1 mm or less.

20. The apparatus of claim 4, wherein the anode is spaced apart from cathode by a distance of 500 microns or less.

* * * * *